(12) United States Patent
Maring et al.

(10) Patent No.: US 10,641,771 B2
(45) Date of Patent: *May 5, 2020

(54) PROTEIN TARGET COMPLEX

(71) Applicants: HQ Medical Netherlands B.V., Rotterdam (NL); Publiekrechtelijk rechtspersoon Academisch Ziekenhuis Leiden h.o.d.n. LUMC, Leiden (NL)

(72) Inventors: Markwin Hendrik Maring, Rotterdam (NL); Clemens Waltherus Gerardus Löwik, Rotterdam (NL); Ermond Reijer Van Beek, Rotterdam (NL)

(*) Notice: Subject to any disclaimer, the term of this patent is extended or adjusted under 35 U.S.C. 154(b) by 119 days.

This patent is subject to a terminal disclaimer.

(21) Appl. No.: 14/377,146

(22) PCT Filed: Feb. 6, 2013

(86) PCT No.: PCT/NL2013/050067
§ 371 (c)(1),
(2) Date: Aug. 6, 2014

(87) PCT Pub. No.: WO2013/119114
PCT Pub. Date: Aug. 15, 2013

(65) Prior Publication Data
US 2015/0004626 A1  Jan. 1, 2015

(30) Foreign Application Priority Data
Feb. 6, 2012 (NL) ..................... 2008241

(51) Int. Cl.
| | | |
|---|---|---|
| *G01N 33/533* | (2006.01) | |
| *G01N 33/569* | (2006.01) | |
| *G01N 33/50* | (2006.01) | |
| *A61K 31/352* | (2006.01) | |
| *A61K 31/403* | (2006.01) | |
| *A61K 31/404* | (2006.01) | |
| *C07K 14/435* | (2006.01) | |
| *G01N 33/574* | (2006.01) | |
| *G01N 33/58* | (2006.01) | |
| *C07D 209/24* | (2006.01) | |
| *C07D 498/14* | (2006.01) | |
| *C07D 498/22* | (2006.01) | |

(52) U.S. Cl.
CPC ..... *G01N 33/56966* (2013.01); *A61K 31/352* (2013.01); *A61K 31/403* (2013.01); *A61K 31/404* (2013.01); *C07D 209/24* (2013.01); *C07D 498/14* (2013.01); *C07D 498/22* (2013.01); *C07K 14/435* (2013.01); *G01N 33/5008* (2013.01); *G01N 33/5091* (2013.01); *G01N 33/533* (2013.01); *G01N 33/57496* (2013.01); *G01N 33/583* (2013.01); *G01N 2500/10* (2013.01); *G01N 2510/00* (2013.01); *G01N 2800/52* (2013.01)

(58) Field of Classification Search
CPC ......... G01N 33/56966; G01N 33/5008; G01N 33/5091; G01N 33/57496; G01N 33/583; G01N 33/533; G01N 2500/10; G01N 2510/10; G01N 2800/52; A61K 31/352; A61K 31/403; A61K 31/404; C07K 14/435; C07D 209/24; C07D 498/14; C07D 498/22
See application file for complete search history.

(56) References Cited

U.S. PATENT DOCUMENTS

| | | | | |
|---|---|---|---|---|
| 6,974,873 | B2* | 12/2005 | Leung ............... | A61K 41/0057 548/455 |
| 2010/0034800 | A1* | 2/2010 | Kung ................. | C12Q 1/32 424/94.6 |
| 2010/0284922 | A1* | 11/2010 | Cordeiro ........... | A61K 49/0004 424/9.1 |
| 2015/0010921 | A1* | 1/2015 | Maring .............. | G01N 33/5008 435/7.8 |
| 2016/0106851 | A1* | 4/2016 | Maring .............. | A61K 49/0032 424/9.6 |

OTHER PUBLICATIONS

Levelt et al. Streptavidin-Tricolor is a Reliable Marker for Nonviable Cells Subjected to Permeabilization or Fixation. Cytometry 15: 84-86 (1994).*
International Search Report issued in connection with PCT/NL2013/050067, May 13, 2013.
International Preliminary Report on Patentability issued in connection with PCT/NL2013/050067, May 13, 2013.
Written Opinion of the International Searching Authority issued in connection with PCT/NL2013/050067, Aug. 12, 2014.
Hashimoto et al., "Atypical X-linked agammaglobulinemia diagnosed in three adults", Internal Medicine, vol. 38, No. 9, Sep. 1999, pp. 722-725.
Vyakarnam et al., "A comparative nuclear localization study of galectin-1 with other splicing components", Experimental Cell Research, vol. 242, No. 2, Aug. 1, 1998, pp. 419-428.
Prajjapati et al., "near Infrared Imaging of Injured Tissue in Living Subjects using IR-820", Mol Imaging, vol. 8, No. 1, Jan.-Feb. 2009, pp. 45-54.
Perfetto et al., "Amine reactive dyes: An effective tool to discriminate live and dead cells in polychromatic flow cytometry," Journal of Immunological Methods, 313 (2006) 199-208.

* cited by examiner

*Primary Examiner* — Gailene Gabel
(74) *Attorney, Agent, or Firm* — Akerman LLP

(57) ABSTRACT

The present invention relates to a method for labeling or targeting cells whose plasma membrane has lost integrity, such as dead cells, such as for discriminating between live cells and cells whose plasma membrane has lost integrity; to an embodiment of the method for determining one or more values of one or more parameters of cells of a biological sample; to use of the method in an assay for screening drugs for therapy such as cancer therapy; to use of the method to monitor and/or determine the effectiveness of a therapy; to an assay kit; to a complex; to the complex for use as a medicament; to the complex for use in treatment of cancer(s) and/or plaque(s) and/or regeneration and/or supporting the immune system; and, to a dead cell.

9 Claims, 9 Drawing Sheets

Fig. 1
Fig. 1a
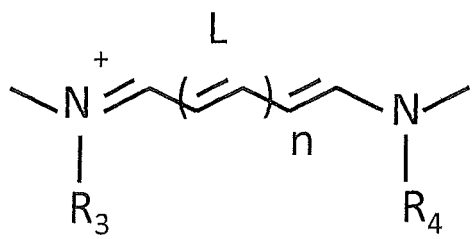
I
Fig. 1b
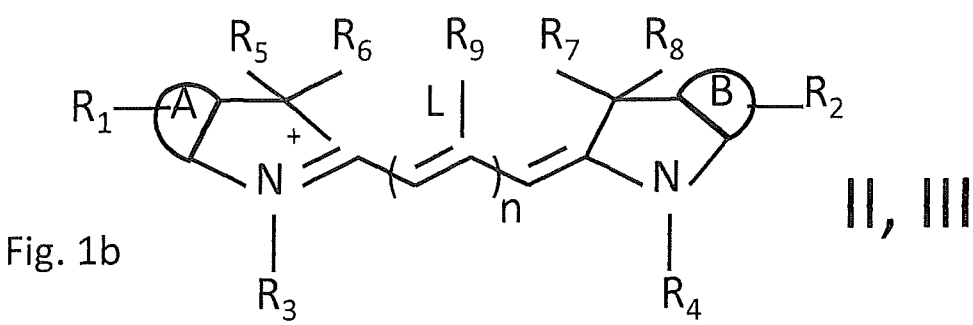
II, III
Fig. 1c
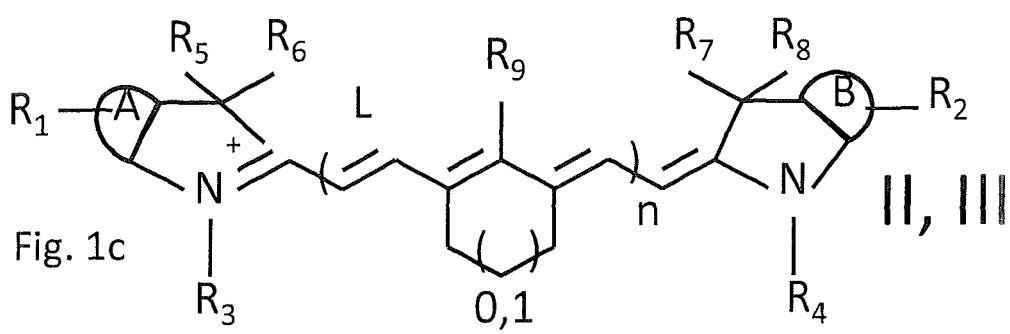
II, III
Fig. 2
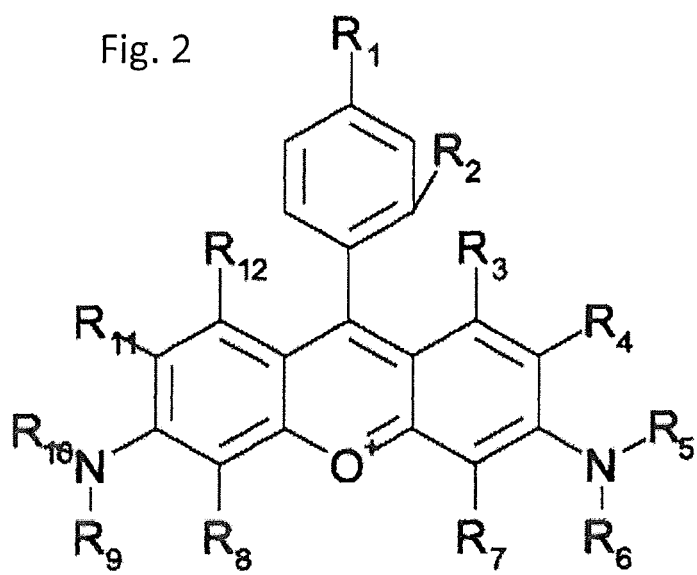
Fig. 1d
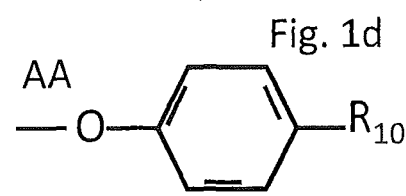
AA
Fig. 1e
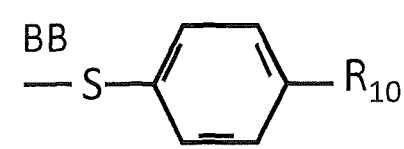
BB (a)

HQ5 staining     TUNEL staining (b)

HQ5 staining     TUNEL staining (c)

HQ5 staining     TUNEL staining

PROTEIN TARGET COMPLEX

This application is a national phase of PCT/NL2013/050067, filed Feb. 6, 2013, and claims priority to NL 2008241, filed Feb. 6, 2012, the entire contents of both of which are hereby incorporated by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

Field of the Invention (Technical Field)

The present invention is in the field of labeling and/or targeting cells whose plasma membrane has lost integrity, such as dead cells.

Description of Related Art

Excessive cell death is characteristic of vascular disorders, neurodegenerative diseases, myelodysplastic syndromes, ischemia/reperfusion injury and organ transplant rejection, among others. Cell death also plays a role in the treatment of disease. In cancer, for example, most chemotherapeutics, radiation treatments and anti-hormonal agents act by inducing death of cancer cells.

Cell death plays an important role in development and normal tissue- or cell turnover like e.g. skin, gut, hair, and in the reproductive and immune system. Under normal physiological conditions cell death is strictly regulated and an imbalance is usually associated with diseases, like e.g. ischemia-reperfusion injury as can occur after stroke or myocardial infarction, neurodegenerative diseases, myelodysplastic diseases, rejection after transplantation of organs or cells, vascular diseases and psoriasis. Cell death, predominantly necrosis, can also occur after trauma or complete (local) lack of oxygen. Cell death also plays a role in the treatment of disease. In cancer, for example, most chemotherapeutics, radiation treatments and anti-hormonal agents act by inducing death of cancer cells.

Since cell death plays such an important role in many diseases, non-invasive imaging and targeting of dead cells in a biological sample comprising a population of cells is highly desirable and needed e.g., as a diagnostic tool for early detection and progression of diseases and to follow therapeutic effects of therapies. This will allow not only to determine the degree of tissue injury after e.g. myocardial infarction or stroke and to identify vulnerable plaques in atherosclerosis but also e.g. to monitor treatment response in cancer.

A useful document on the classification of cell death has been published by Kroemer et al. (Cell Death Differ, 2009, 16(1), 3-11). For the purposes of the present document, a dead cell is defined in accordance with a recommendation of this document as a cell whose plasma membrane has lost integrity, as defined by the incorporation of vital dyes, e.g. propidium iodide (PI).

Methods for staining dead cells are known in the prior art. Such methods typically relate to the use of cell-impermeant fluorescent compounds that are able to stain nucleic acids. In healthy cells the dye and cellular DNA are kept separate by the cell membrane, the nuclear membrane and the mitochondrial membranes; only upon cell death do these membranes become permeable such that DNA and the dye can come into contact. The fluorescence intensity is proportional to the number of dead cells in the population. Disadvantages of targeting DNA are typically mutagenic, and therefore toxic.

An alternative method has been demonstrated by the group of M. Roederer wherein amine reactive dyes are used to discriminate between live and dead cells. Fluorescent amine reactive dyes will nonspecifically bind to membrane proteins on live cells. However, in dead or dying cells, where the cell membrane is disrupted, the fluorescent amine reactive dyes aspecifically bind to the highly abundant intracellular proteins resulting in an increased fluorescent signal shown by flow cytometry. (Perfetto S P et al., J. Immunol. Methods. 2006, 313(1-2), 199-208)

Disadvantages of the use of amine-reactive dyes for discriminating between live and dead cells are that the dyes will also react with any other amines present in the medium comprising the cells, such as serum components and extracellular proteins. Furthermore such compounds are typically unstable and degrade over time.

It is an object of the invention to overcome one or more problems of the methods of the prior art and to provide an alternative thereto.

SUMMARY OF THE INVENTION

The present invention relates to a method for labeling or targeting cells whose plasma membrane has lost integrity, such as dead cells, such as for discriminating between live cells and cells whose plasma membrane has lost integrity; to an embodiment of the method for determining one or more values of one or more parameters of cells of a biological sample; to use of the method in an assay for screening drugs for therapy such as cancer therapy; to use of the method to monitor and/or determine the effectiveness of a therapy; to an assay kit; to a complex; to the complex for use as a medicament; to the complex for use in treatment of cancer(s) and/or plaque(s) and/or regeneration and/or supporting the immune system; and, to a dead cell.

The method may be performed in vivo, in vitro, in a dead organism, or any other way.

DETAILED DESCRIPTION OF THE INVENTION

In a first aspect, the invention relates to a method for labeling or targeting cells whose plasma membrane has lost integrity, such as dead cells, such as for discriminating between live cells and cells whose plasma membrane has lost integrity, wherein the method comprises: (a) providing a population of cells comprising cells whose plasma membrane has lost integrity, and a first intracellular protein; (b) providing a first non-activated extracellularly applied first compound (e.g. a compound capable of interacting chemically/physically/biologically with the first protein), wherein the first compound is substantially unable to cross a healthy cell membrane; (c) chemically/physically/biologically interacting the first compound and the first protein in a cell whose plasma membrane has lost integrity, such as a dead cell, and (d) performing a measurement to determine an amount of interaction between the first compound and the cell whose plasma membrane has lost integrity.

The terms labelling and targeting are commonly used in the field of the invention and are given their usual meaning as would be understood by a person of skill in the art.

A compound that is substantially unable to cross a healthy cell membrane is a compound that if applied to a population of cells (e.g. in culture, e.g. a population of tissue cells), would not be considered by a person skilled in the art to be cell permeant e.g. it cannot cross an intact plasma membrane. If the compound is fluorescent, such can be determined by e.g. microscopy; for non-fluorescent compounds, possibilities include labelling the compound.

The terms intracellular and extracellular relate to being inside and outside of the plasma membrane of a cell respectively. The intracellular protein is preferably not a membrane protein. The intracellular protein is present inside cells of the present population of cells. An extracellularly applied compound is e.g. a compound provided on the population of cells, e.g. into a culture medium.

The term non-activated is commonly used in the field of bio-conjugation; the term is used in the present application in the same way. Activated compounds are compounds that have been chemically modified to increase or introduce chemical reactivity towards certain functional groups, in particular, alcohols, amines and thiols, or compounds which are inherently reactive thereto because of the native functional groups of the compound. Most commonly, carboxylic acids are activated to increase their reactivity towards amines. In short, a non-activated compound is a compound that would be considered by a person skilled in the art to be substantially unreactive towards functional groups including carboxylic acids, alcohols, amines and thiols under conditions commonly used for labelling biomolecules. The first compound does not comprise functional groups such as maleimides, N-hydroxy succinimide, N-hydroxysulfosuccinimide, 4-Sulfo-2,3,5,6-Tetrafluorophenol (STP), thiocyanates, isothiocyanates, hydrazines, aldehydes, alkyl halides, active esters etc. The first compound does not comprise functional groups that, in a biological sample, e.g. in aqueous medium, e.g. comprising proteins, would substantially react covalently therewith i.e. the compound is able to diffuse through the biological sample without undergoing covalent interaction. As an example the first compound may be a dye compound having only a carboxylic acid functional group, such is a non-activated compound since it cannot be used for labelling biomolecules. This is in contrast to maleimide and/or N-hydroxysuccinimide derivatives thereof.

The term chemically/physically/biologically interact is used to broadly define that the first compound and the first protein interact in some way, e.g. through a chemical, physical and/or biological interaction, such as through a chemical (covalent) bond (not preferred), in ionic interaction, a van der Waals interaction, a pi-stacking interaction, intercalation, specific or non-specific biding to binding domains or sub domains of proteins etc. Of relevance is that the protein and the compound interact such that the complex of the protein and the compound can be detected, that is to say that the interaction is not transient. The term complex is used to refer to a protein having at least the compound bound thereto.

In a simple embodiment, determining an amount of interaction (e.g. performing a measurement to determine an amount of interaction) relates to confirming that the first compound is inside a cell. If the compound is fluorescent, such can be achieved by imaging, such as by fluorescence and/or confocal microscopy.

In a further simple embodiment, it is sufficient to detect a signal from the first compound or a label of the first compound. For many techniques the signal is only detectable, or only exceeds a particular reference value if a sufficient quantity of compound has localized at a particular location in a sample.

The first protein is considered to be a part of the cell whose plasma membrane has lost integrity.

In an example, the first protein is selected from a group comprising fibrous proteins, such as 40 kDa proteins, 100 kDa proteins, such as tubulin, such as α-tubulin, β-tubulin, γ-tubulin, δ-tubulin and ε-tubulin, actin, such as G-actin, and F-actin, fibrous structural proteins, such as keratin, such as neutral, basic or acidic keratin, such as keratin 1-keratin 20, metalloenzymes, such as enolase, and lyase, CDC37, preferably tubulin or actin, isomers thereof, complexes thereof, and decay products thereof.

The above identified proteins are prevalent in cells and only become accessible to the first compound upon loss of integrity of the cell membrane. As such they are particularly suitable targets. Tubulin and actin are among the most prevalent proteins in cells.

In an example, the first compound is selected from one or more of: a compound capable of interacting chemically/physically/biologically with the first protein; a fluorescent compound, such as a cyanine, a rhodamine, and a conjugate thereof (e.g. a cyanine or rhodamine coupled to a further compound), preferably non-activated or de-activated compound, such as a carboxylate thereof; an active compound, such as: (i) a therapeutic compound, such as a medicament, (ii) a reporter compound such as a tracer, such as a radioactive tracer, a chemotherapeutic, an MRI contrast agent, a microbubble for ultrasound or opto-acoustic imaging, a nanoparticle such as a quantum dot, a biological active compound, and a molecule suitable for imaging; and a vehicle for transport of the active compound. The first compound is a compound that if brought together with the first protein is able to interact therewith, that is to say binds in some way thereto such that an interaction between the bound pair (complex) can be determined. It has been found experimentally that certain combinations of the present first compounds (two or more) have superior interaction characteristics.

In an example, the first compound is a reporter compound such as a compound that is amenable to detection by one or more techniques selected from a group consisting: optical spectroscopies, optical microscopy, acoustical imaging, acoustic spectroscopies, MRI, PET, SPECT, CT, and combinations thereof.

Examples of the above relate to e.g. a first compound comprising a chelating moiety (e.g. DOTA-like moieties) that can bind an isotope or the like, such as $^{111}In^{3+}$, making the method suitable for SPECT. Likewise an isotope, such as $^{18}F$, may be used, making the method suitable for PET. Likewise and isotope as $^{19}F$, may be used, making the method suitable for MRI.

In an example, the first compound is a non-activated cyanine and/or rhodamine, preferably a cyanine according to FIG. 1 I, II and III, wherein n is an integer, such as n∈[2,10], preferably n∈[4,8], the chain L has up to n−1 double bonds, preferably n/2 double bonds, wherein sub-families II and III may comprise respectively one and two aromatic ring systems (A,B) signified by the curved line(s) C, wherein A,B are preferably selected each individually from benzene and naphthalene, wherein further groups $R_5$, $R_6$, $R_7$, and $R_8$, may be present, $R_5$, $R_6$, $R_7$, and $R_8$, are preferably selected each individually from H, and alkyl, such as methyl, ethyl, and propyl, preferably methyl, wherein the aromatic ring systems may comprise further functional groups $R_1$, $R_2$, and/or substituents, $R_1$, $R_2$, are preferably selected each individually from H, sulfonate, and sulfonamide, wherein the chain of alternating single and double bonds L may be interrupted by one or more partly and fully saturated ring structures, such as cyclopentene and cyclohexene, and combinations thereof, such as one or more cyclohexene rings, wherein the saturated ring structure may further comprise functional groups $R_9$, $R_9$ being selected from H, AA and BB, wherein $R_{10}$ is selected from, H, $SO_3H$, Cl, —N=C=O—$(CH2)_q$—$Y_3$ (q=1-6), —$(CH2)_r$—$Y_4$ (r=1-6), $Y_3$ and $Y_4$ are each independently one of H, COOH, $SO_3H$, CN, wherein the nitrogen atoms (N) may comprise further functional N-side groups $R_3$, $R_4$, wherein $R_3$, $R_4$ are preferably selected each individually from —$(CH_2)_m$Y, wherein Y is selected each individually from a carboxylic acid having 1-4 carbon atoms, a sulfonate group, CN, C≡C, and C=C, and salts thereof, wherein said N-side groups comprise m carbon atoms, such as m∈[1,10], preferably m∈[2,8], more preferably m∈[3,7], most preferably m∈4, 5, and 6, even more preferably at least one of m=4, 5, and 6, preferably one m=6, and the other m preferably is 4, 5 or 6, wherein said N-side groups comprise one or more functional groups on an end opposing the N, such as a carboxylic acid having 1-4 carbon atoms, an sulfonic group, and salts thereof, such as sodium and potassium salts, most preferably the functional group on the end comprises one or more double C—C bonds, such as one of HQ4, HQ5, HQ6, HQ7, ICG, CW 800, ZW800, L4, L7, L11, CY3, CY3b, CY3.5, CY5, CY5.5, CY7, Dy 676, Dy 681, Dy 731, Dy 751 and Dy 776, preferably a carboxylate thereof, preferably HQ4 or HQ5.

The structures of these compounds are given in the Drawings.

HQ4, HQ5, HQ6, HQ7, ICG, CW 800, ZW800, L4, L7, L11, CY3, CY3b, CY3.5, CY5, CY5.5, CY7, Dy 676, Dy 681, Dy 731, Dy 751 and Dy 776 are examples of fluorescent compounds that are unable to cross the plasma membranes of healthy cells, but which enter into cells whose plasma membrane has lost integrity, such as dead cells, and which interact with proteins such as actins and tubulins. Furthermore, these compounds have desirable photophysical properties from the point of view of their use as labels, e.g. high fluorescence quantum yield, low susceptibility to quenching etc.

In a second aspect, the invention relates to an embodiment of the method, wherein the method further comprises: (e) performing one or more further measurements on the sample with a first technique suitable for detecting the first compound to provide a value or values of the first compound;

(f) analysing the value or values to determine one or more values of the one or more parameters of the cells whose plasma membrane has lost integrity of the biological sample, and;

(g) optionally repeating (d) and/or, (e) and (f) for a given sample at multiple time-points to determine a change in the value of a parameter, or the amount of interaction, as a function of time.

Advantageously, in addition to determining an amount of interaction, further values of parameters can be determined. Through optional steps (g), which in a preferred embodiment are not optional, the change in a parameter as a function of time may be determined. Such can be used e.g. for monitoring a treatment in vivo or monitoring the effectiveness of a particular compound in vitro.

In an example of the method for determining one or more values of one or more parameters of cells of a biological sample, a value or values above a threshold value indicate binding of the compound to the first cell protein.

In an example of the method for determining one or more values of one or more parameters of cells of a biological sample, the one or more parameters is the presence and/or concentration and/or location of cells whose plasma membrane has lost integrity in the population of cells.

In a third aspect, the invention relates to use of the method in an assay for screening drugs for therapy such as cancer therapy.

In a fourth aspect, the invention relates to use of the method in a diagnostic method, or to monitor and/or determine the effectiveness of a therapy.

In a fifth aspect, the invention relates to an assay kit comprising a fluid, such as a physiological fluid, a first nonactivated compound that if brought together with the first intracellular protein is able to interact chemically/physically/biologically therewith, wherein the first compound is one or more of: an active compound, such as: (i) a therapeutic compound, such as a medicament, (ii) a reporter compound such as a tracer, such as a radio-active tracer, a chemotherapeutic, an MRI contrast agent, a microbubble for ultrasound or opto-acoustic imaging, a nanoparticle such as a quantum dot, a biological active compound, and a molecule suitable for imaging; and a vehicle for transport of the active compound, a means for storing, a means for transferring, and any further suitable product.

In a sixth aspect, the invention relates to use of a cyanine and/or rhodamine for discriminating between live cells and cells whose plasma membrane has lost integrity, wherein the cyanine and/or rhodamine is a non-activated cyanine and/or rhodamine, preferably a cyanine according to FIG. 1 I, II and III, wherein n is an integer, such as n∈[2,10], preferably n∈[4,8], the chain L has up to n−1 double bonds, preferably n/2 double bonds, wherein sub-families II and III may comprise respectively one and two aromatic ring systems (A,B) signified by the curved line(s) C, wherein A,B are preferably selected each individually from benzene and naphthalene, wherein further groups $R_5$, $R_6$, $R_7$, and $R_8$, may be present, $R_5$, $R_6$, $R_7$, and $R_8$, are preferably selected each individually from H, and alkyl, such as methyl, ethyl, and propyl, preferably methyl, wherein the aromatic ring systems may comprise further functional groups $R_1$, $R_2$, and/or substituents, $R_1$, $R_2$, are preferably selected each individually from H, sulfonate, and sulfonamide, wherein the chain of alternating single and double bonds L may be interrupted by one or more partly and fully saturated ring structures, such as cyclopentene and cylcohexene, and combinations thereof, such as one or more cyclohexene rings, wherein the saturated ring structure may further comprise functional groups $R_9$, $R_9$ being selected from H, AA and BB, wherein $R_{10}$ is selected from, H, $SO_3H$, Cl, —N—C=O—$(CH2)_q$—$Y_3$ (q=1-6), —$(CH2)_r$—$Y_4$ (r=1-6), $Y_3$ and $Y_4$ are each independently one of H, COOH, $SO_3H$, CN, wherein the nitrogen atoms (N) may comprise further functional N-side groups $R_3$, $R_4$, wherein $R_3$, $R_4$ are preferably selected each individually from —$(CH_2)_mY$, wherein Y is selected each individually from a carboxylic acid having 1-4 carbon atoms, a sulfonate group, CN, C≡C, and C=C, and salts thereof, wherein said N-side groups comprise m carbon atoms, such as m∈[1,10], preferably m∈[2,8], more preferably m∈[3, 7], most preferably m=4, 5, and 6, even more preferably at least one of m=4, 5, and 6, preferably one m=6, and the other m preferably is 4, 5 or 6, wherein said N-side groups comprise one or more functional groups on an end opposing the N, such as a carboxylic acid having 1-4 carbon atoms, an sulfonic group, and salts thereof, such as sodium and potassium salts, most preferably the functional group on the end comprises one or more double C—C bonds, such as one of HQ4, HQ5, HQ6, HQ7, ICG, CW 800, ZW800, L4, L7, L11, CY3, CY3b, CY3.5, CY5, CY5.5, CY7, Dy 676, Dy 681, Dy 731, Dy 751 and Dy 776, preferably a carboxylate thereof, preferably HQ 4 or HQ5.

In a seventh aspect, the invention relates to a complex, such as for discriminating between live cells and cells whose plasma membrane has lost integrity, of the first compound and the first protein obtainable by the method of the invention.

In an example, the complex is characterized by a ratio of an amount of first compound being bound to a given quantity of cells whose plasma membrane has lost integrity divided by an amount of first compound being bound to a same given quantity of living cells ([amount dead cell]/[amount living cell]), wherein the ratio is larger than 10, preferably larger than $10^2$, more preferably larger than $10^5$, even more preferably larger than $10^7$, such as larger than $10^9$.

In an eighth aspect the invention relates to use of a complex according to aspect six of the invention for discriminating between live cells and cells whose plasma membrane has lost integrity.

In a ninth aspect the invention relates to the complex for detecting radiation.

In an tenth aspect, the invention relates to the complex use as a medicament.

In a eleventh aspect the invention relates to the complex for use in treatment of cancer(s) and/or plaque(s) and/or regeneration and/or supporting the immune system.

In a twelfth aspect, the invention relates to a dead cell comprising the first compound and the first protein obtainable by the method of the invention.

The invention will be further elucidated with reference to the Drawings of FIGS. 1-18 and the Example to which FIGS. 6 to 18 relate. The Example and Drawings are provided for illustrative purposes and are not to be considered to limit the invention.

SUMMARY OF FIGURES

FIGS. 1a-e show generic structures of three main sub-families of the present cyanine. Cyanine is a non-systematic name of a synthetic dye family belonging to polymethine group. Referring to the central carbon chain in FIG. 1; n is an integer, such as n∈[2,10], preferably n ∈[4,8], the chain L has up to n−1 double bonds, preferably n/2 double bonds, wherein sub-families II and III may comprise respectively one and two aromatic ring systems (A,B) signified by the curved line(s) C, wherein A,B are preferably selected each individually from benzene and naphthalene, wherein further groups R5, R6, R7, and R8, may be present, R5, R6, R7, and R8, are preferably selected each individually from H, and alkyl, such as methyl, ethyl, and propyl, preferably methyl, wherein the aromatic ring systems may comprise further functional groups R1, R2, and/or substituents, R1, R2, are preferably selected each individually from H, sulfonate, and sulfonamide, wherein the chain of alternating single and double bonds L may be interrupted by one or more partly and fully saturated ring structures, such as cyclopentene and cylcohexene, and combinations thereof, such as one or more cyclohexene rings, wherein the saturated ring structure may further comprise functional groups $R_9$, $R_9$ being selected from H, AA and BB, wherein $R_{10}$ is selected from, H, $SO_3H$, Cl, —N—C=O—$(CH2)_q$—$Y_3$ (q=1-6), —$(CH2)_r$—$Y_4$ (r=1-6), $Y_3$ and $Y_4$ are each independently one of H, COOH, $SO_3H$, CN, wherein the nitrogen atoms (N) may comprise further functional N-side groups $R_3$, $R_4$, wherein $R_3$, $R_4$ are preferably selected each individually from —$(CH_2)_mY$, wherein Y is selected each individually from a carboxylic acid having 1-4 carbon atoms, a sulfonate group, CN, C≡C, and C=C, and salts thereof, wherein said N-side groups comprise m carbon atoms, such as m∈[1,10], preferably m∈[2,8], more preferably m∈[3, 7], most preferably m=4, 5, and 6, even more preferably at least one of m=4, 5, and 6, preferably one m=6, and the other m preferably is 4, 5 or 6, wherein said N-side groups comprise one or more functional groups on an end opposing the N, such as a carboxylic acid having 1-4 carbon atoms, an sulfonic group, and salts thereof, such as sodium and potassium salts. most preferably the functional group on the end comprises one or more double C—C bonds.

The term cyanine refers to any compound whose corestructure is that of sub-family I, II or III. The integer in names of cyanines such as Cy 3, Cy 5, Cy 7 etc. refers to the number of carbon atoms in the chain L. In an exemplary embodiment, the cyanine belongs to one of these families.

FIG. 2 shows a generic structure of a Rhodamine; R1 to R12 can be hydrogen or a functional group, examples of suitable functional groups include sulfonic acid groups, carboxylic acid groups, sulfonamides, alcohols, amines, esters, ethers, thiols, thio esters and combinations thereof. The term Rhodamine refers to any compound whose core-structure is that shown in FIG. 2.

FIG. 3(a)-(j) gives the structures of compounds referred to throughout the application. Where a counterion is shown, this may be for example $H^+$, $Na^+$ or $K^+$.

Figure 3:
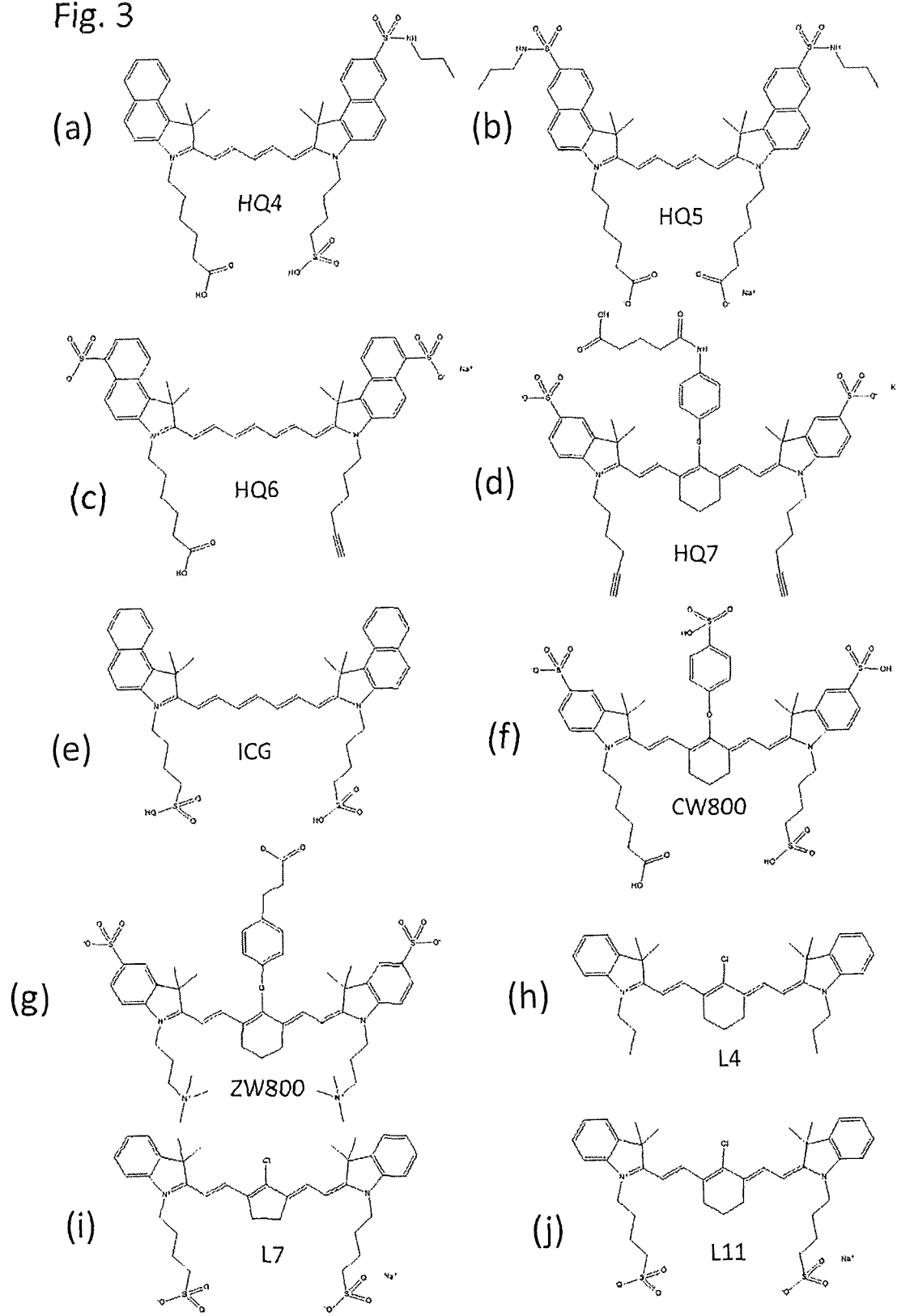
Figure 4:
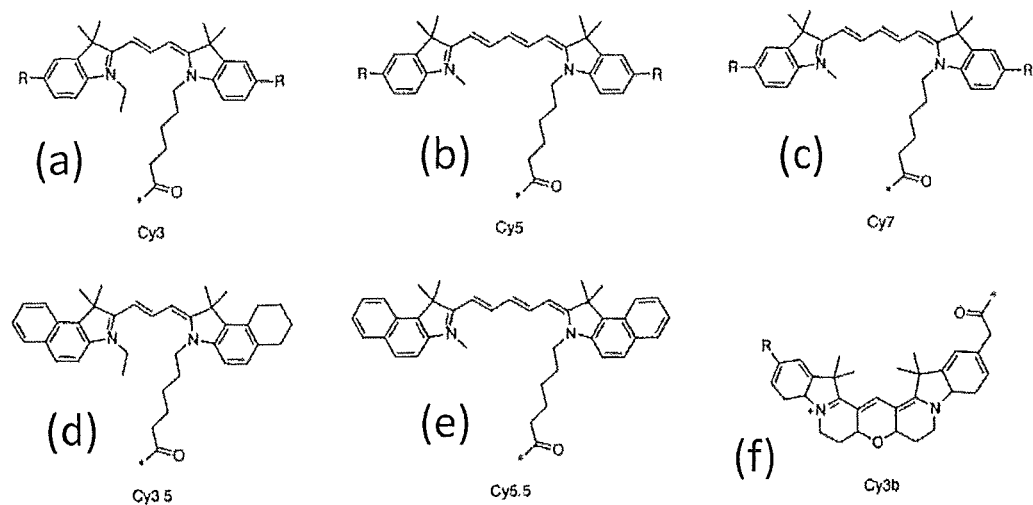
Figure 5:
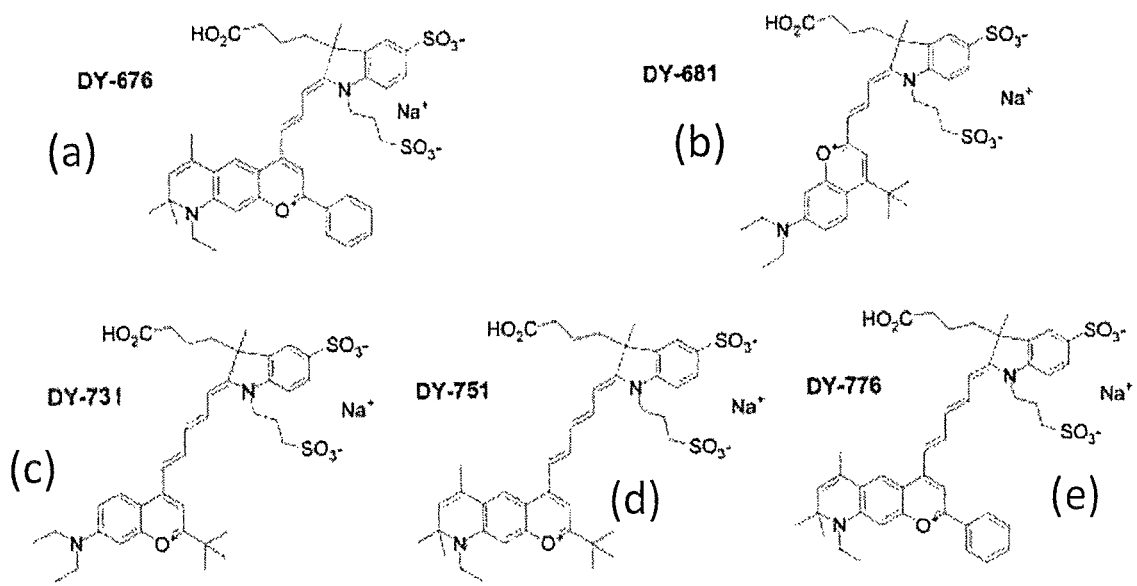
Figure 6:
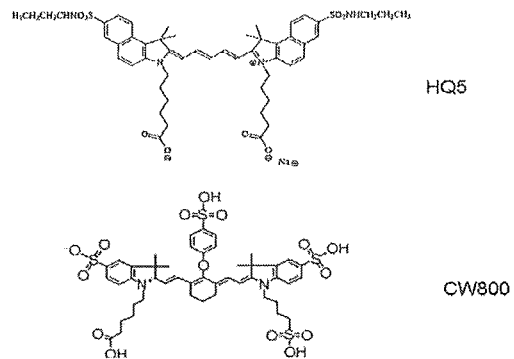
Figure 7:
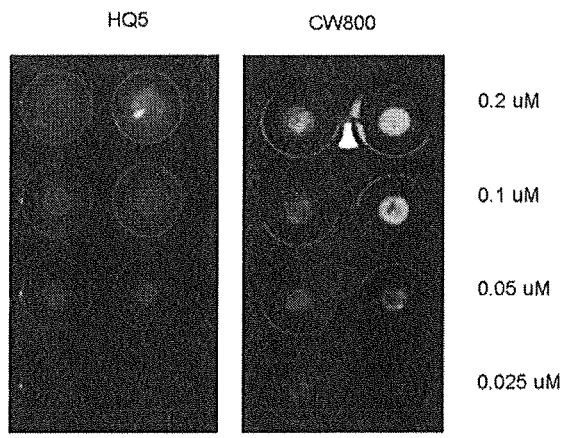
Figure 8:
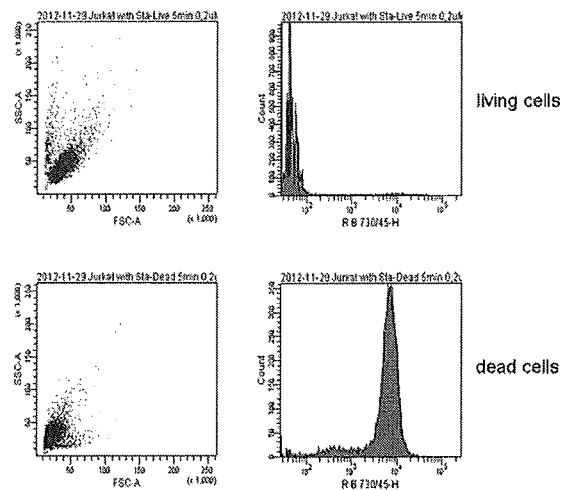
Figure 9:
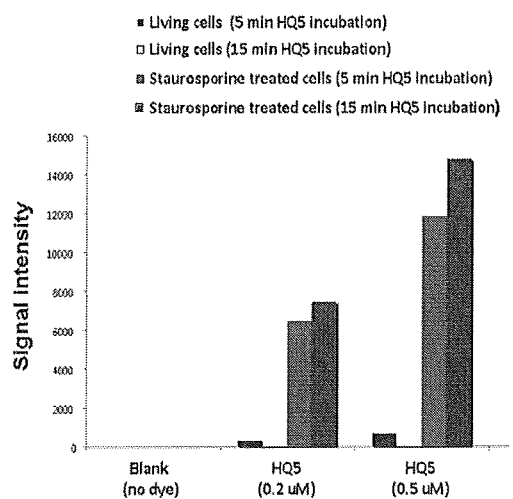
Figure 10:
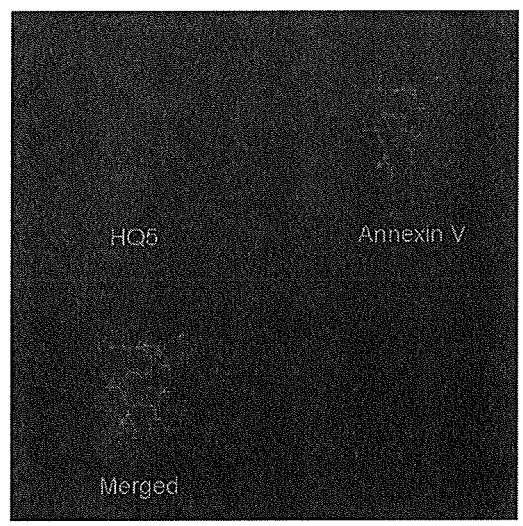
Figure 11:
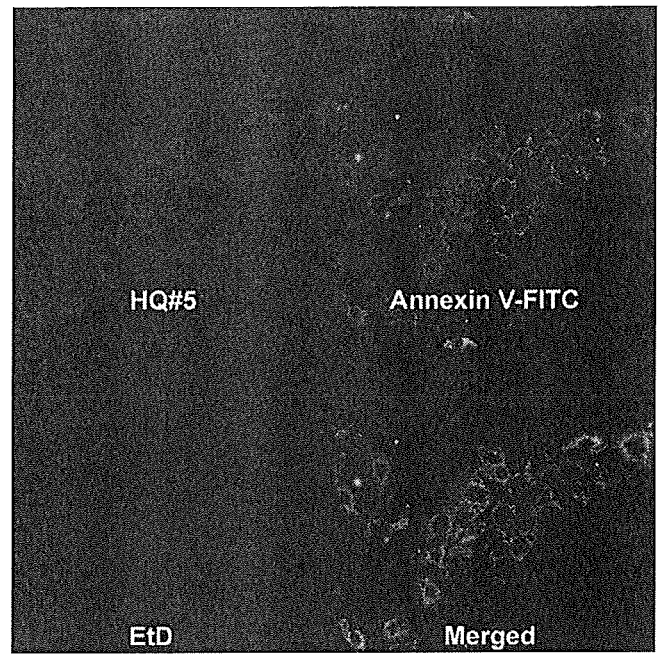
Figure 12:
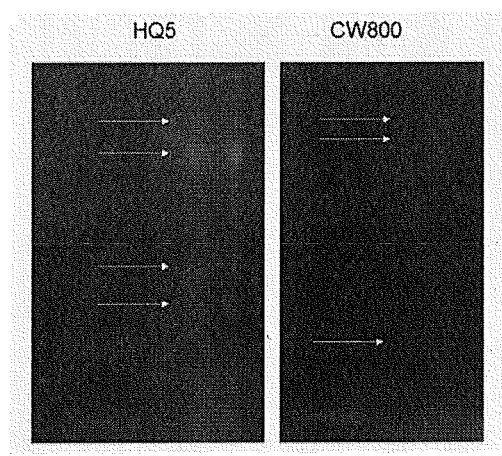
Figure 13:
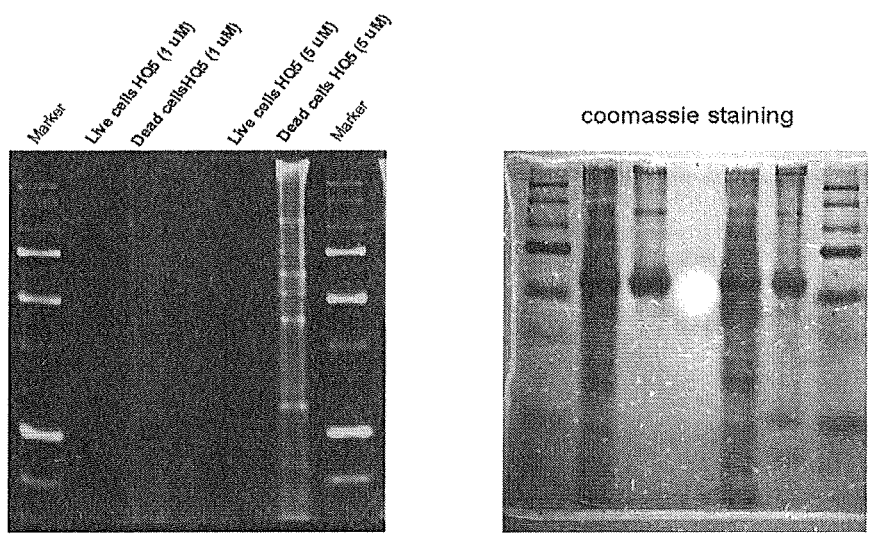
Figure 14:
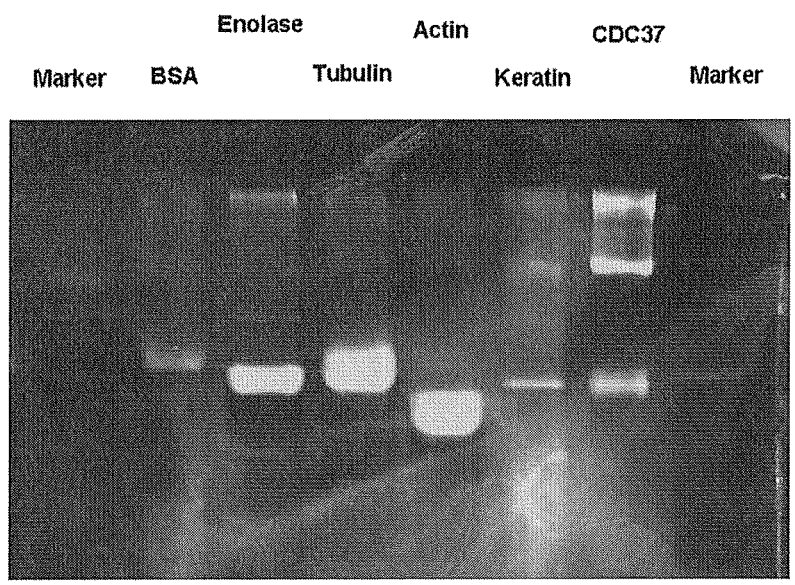
Figure 15:
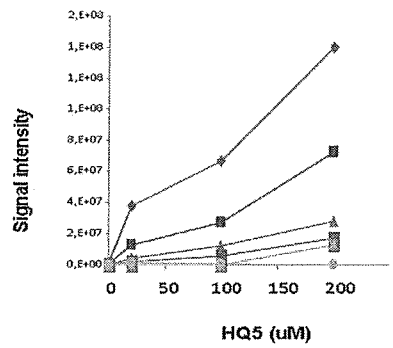
Figure 16:
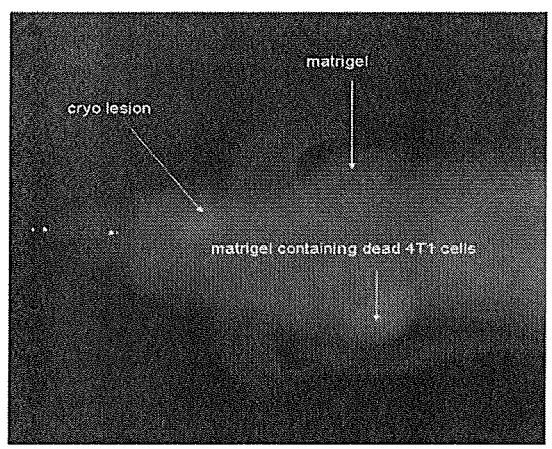
Figure 17:
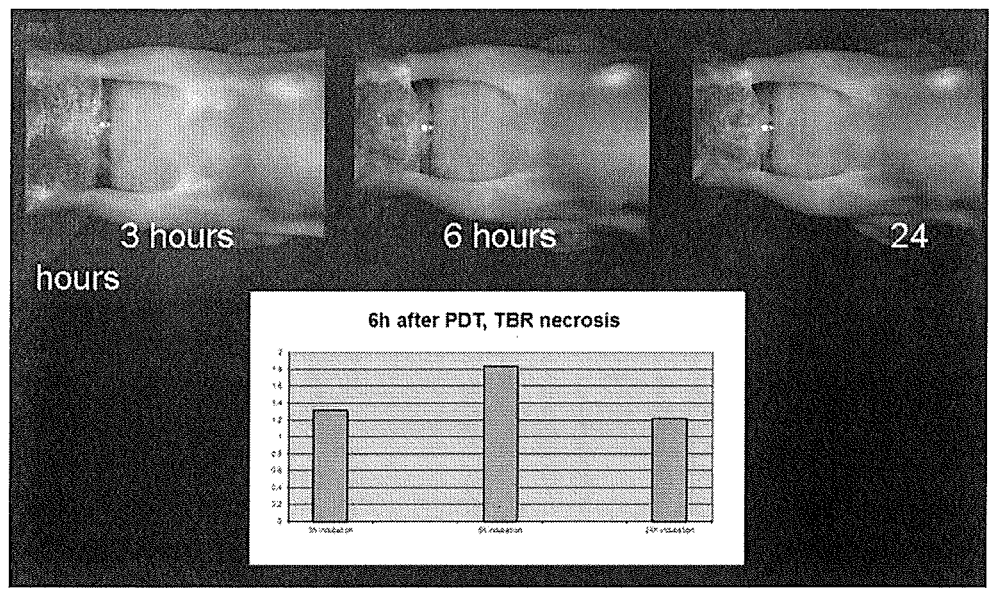

FIGS. 4a-f and 5a-e give further examples of 'first compounds' suitable for the method of the invention. The structures (a)-(j) of FIG. 3 are preferred examples, HQ4 and HQ5 are particularly suitable for the method of the invention. Specifically: FIG. 4 shows structures of Cy3, Cy5, Cy7, Cy3.5, Cy5.5 and Cy3b (R=SO3-, H or alkyl; *=OH); FIG. 5 shows a series of Dy dyes. FIG. 6 shows the chemical structure of HQ5 and CW800. FIG. 7 shows binding of cyanine dyes HQ5 and CW800 to dead cells or uptake by living cells using the dry-ice assay. FIG. 8 shows FACS analysis of living and dead Jurkat cells labelled with HQ5. FIG. 9 is a bar graph representation of the FACS data of FIG. 8. Uptake of HQ5 by dead cells is dose- and time dependent. FIG. 10 shows confocal microscopic pictures of Gambo-gic acid treated 4T1 cells stained with HQ5 or AnnexinV. FIG. 11 shows confocal microscopic pictures of Gambo-gic acid treated 4T1 cells stained with HQ5, Annexin V and EtD. FIG. 12 relates to identification of intracellular proteins that bind HQ5. FIG. 13 shows homogenates of dead and living cells treated with HQ5 (1 and 5 μM) and subsequently run on SDS PAGE. FIG. 14 shows different intracellular ~40 proteins and BSA run on SDS-PAGE and stained with HQ5. FIG. 15 shows saturation curves of HQ5 to dead 4T1 cells, killed by liquid N2. FIG. 16 demonstrates that HQ5 does not indicate dead tissue by acting as a blood pool agent. FIG. 17 shows CW800-PLGA nano-particle targeting tumors after photodynamic therapy. FIG. 18a-c is a histological examination of development of spontaneous necrosis in 4T1 tumors over time.

EXAMPLES/EXPERIMENTS

Example

Selective Binding of Cyanine Dyes to Dead Cells In Vitro and In Vivo
Introduction It has been observed that cyanine dyes of the invention, compounds that are used as controls to parent (bio) molecule coupled dyes to determine potential effects or retention of the dye itself, showed high and selective affinity for dead cells. These carboxylate forms of cyanine dyes, in contrast to their maleimide and NHS ester counterparts do NOT contain reactive groups and cannot be used for labeling (bio) molecules.

It is important to mention that amine reactive dyes cannot be used in vivo because these will immediately and nonselectively covalently bind to all serum- and other proteins in the body that contain a free $NH_2$ (amine) group.

Using HQ5 carboxylate as lead compound, binding specificity to dead cells in vitro in our newly developed dry ice assay and by FACS analysis has been determined. Moreover, using confocal microscopy and specific markers of early- and late stage cell death it has been established at which phase cyanine dyes bind to dead/dying cells. In addition, the mechanism and the intracellular target proteins to which these cyanine carboxylates bind to in dead cells has been identified.

In vivo, using mice bearing a cryo lesion and matrigel, containing dead cells, it has been shown that HQ5 extravasates through intact vessels and does not merely acts as a blood pool agent. In relation to this it is important to mention the paper of the group of C. Keller where they describe the cyanine dye IR-820 to image injured tissues. However, they show that IR-820 is a blood pool agent that just simply leaks out of blood vessels after disruption of the vessels. (Prajapati S I, Martinez C O, Bahadur A N, Wu I Q, Zheng W, Lechleiter J D, McManus L M, Chisholm G B, Michalek J E, Shireman P K, Keller C. Near-infrared imaging of injured tissue in living subjects using IR-820. Mol Imaging. 2009 January-February; 8(1):45-54.)

Finally, using mice transplanted with the fast growing 4T1-luc2 mouse breast tumor, we showed that HQ5 specifically labeled necrotic areas in the tumors. These necrotic areas arise spontaneously during tumor development due to insufficient blood supply as a result of the fast growth rate.
Method
Dry Ice Assay 4T1-Luc cells were seeded onto individual wells from a 12-well cell culture plate and allowed to grow to confluence in RPMI media supplemented with 10% fetal bovine serum. 4T1-luc2 mouse breast cancer cells were used as the adherence of these cells to the bottom of the culture well remains strong after dry-ice treatment. To initiate cryo-induced cell death, media was discarded and dry-ice was applied to the bottom center of each individual well for 15 sec. Subsequently, fresh medium with different concentrations of the first compound of the invention were added and cells were incubated at 37° C. for 15 min. After incubation, the media were discarded and the cells were washed twice with serum free medium and 0.5 ml fresh RPMI was added to each well. Cells were then visualized using a Licor Odyssey equipped with 700 and 800 nm diode laser. Luciferin (1.25 mg/kg) was also added to each well and fluorescence and bioluminescence images were acquired using an IVIS Spectrum (fluorescence: excitation filter: 710 nm, emission filter: 820 nm, exposure time: 90 s, bin: 8, f/stop: 2, field of view: 12.9 cm) (bioluminescence: open filter, exposure time: 30 s, bin: 8, f/stop: 1, field of view: 12.9 cm). Some culture wells were also stained for 15 min with Trypan Blue (0.2% in culture medium) to confirm cell death.
Results With reference to FIGS. 6 to 18.

FIG. 6 shows chemical structures of cyanine dyes HQ5 and CW800 which were used in the experiments of the example.

FIG. 7 shows binding of cyanine dyes HQ5 and CW800 to dead cells or uptake by living cells using the dry-ice assay.

The carboxylate cyanine dyes HQ5 and CW800 specifically and dose-dependently bind to dead cells in the center of the wells.

FIG. 8 shows FACS analysis of living and dead Jurkat cells labelled with HQ5. FACS analysis of living and Staurosporine treated Jurkat cells incubated with HQQ shows that HQ5 specifically labels dead and not living cells.

FIG. 9 is a bar graph representation of the FACS data of FIG. 8. Uptake of HQ5 by dead cells is dose- and time dependent.

FIG. 10 shows confocal microscopic pictures of Gambogic acid treated 4T1 cells stained with HQ5 or AnnexinV. Gambogic acid kills cells leading to membrane disruption. It is shown that HQ5 stains the cytoplasm of the cells and not the cell nuclei of late apoptotic or necrotic 4T1 cells. Annexin-V-FITC specifically binds to phosphatidyl serine (PS) expressed on the outside of the cell membrane of apoptotic and necrotic cells.

FIG. 11 shows confocal microscopic pictures of Gambogic acid treated 4T1 cells stained with HQ5, Annexin V and EtD. Both HQ5 and EtD can not cross membranes of living cells. However, when the cell membrane is disrupted, for instance as in late stage apoptotic or necrotic cells, HQ5 stains the cytoplasm and EtD binds to DNA in the cell nucleus. We show that HQ5 and EtD staining co-localizes, indicating late apoptotic or necrotic cells. Annexin V, however, can next to late apoptotic and necrotic cells also stain cells in an early stage of apoptosis. For this Annexin V stains a larger number of cells than both HQ5 and EtD.

FIG. 12 relates to identification of intracellular proteins that bind HQ5. In order to try to identify the protein to which the HQ-dyes bind Lysate is (after pre-treatment) incubated with HQ5 and CW800. Exact protocol and technique not specified. HQ5 and CW800 share some but also have different proteins they bind with. A specific HQ5-binding protein has a molecular weight of approx. 40 kD.

FIG. 13 shows homogenates of dead and living cells treated with HQ5 (1 and 5 μM) and subsequently run on SDS PAGE. It is demonstrated that HQ5 specifically binds to certain intracellular proteins in dead cells whereas it does not bind to living cells. One of the prominent bands that are stained both by HQ5 and CW800 is one of 40 kD. This band was cut out of the gel and analysed by mass spectrometry. This analysis revealed that this 40 K protein band contains proteins that are most abundant in cells, including actin and tubulin.

FIG. 14 shows different intracellular~40 proteins and BSA run on SDS-PAGE and stained with HQ5.

FIG. 15 shows saturation curves of HQ5 to dead 4T1 cells, killed by liquid $N_2$. It is shown that up to a HQ5 concentration of 200 µM, no saturation is reached.

FIG. 16 demonstrates that HQ5 does not indicate dead tissue by acting as a blood pool agent. Specifically, FIG. 16 is an image of a HQ5 injected mouse containing a brain cryo lesion and subcutaneous injected matrigel and matrigel containing dead 4T1 cells. At the site of brain cryo lesion blood vessels are massively destructed whereas ate the sites of matrigel injection the blood vessels are fully intact. The fact that dead cells in the matrigel stain with HQ5 suggests that this dye can extravasate through intact vessels and does not merely act as a blood pool agent.

FIG. 17 shows CW800-PLGA nano-particle targeting tumors after photodynamic therapy. Nude mouse bearing two 4T1 breast cancer tumors of which one (upper) was treated with photodynamic therapy. The mouse was injected with nano-particles and imaged 3, 6 and 24 hours after probe injection.

Figure 18:
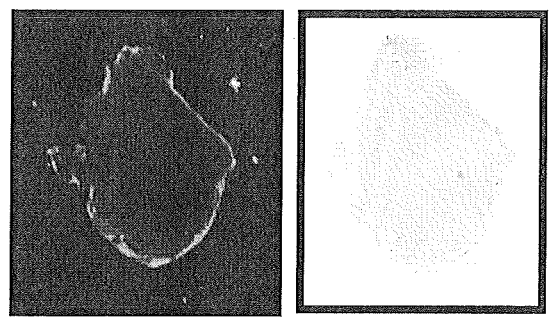
Figure 18:
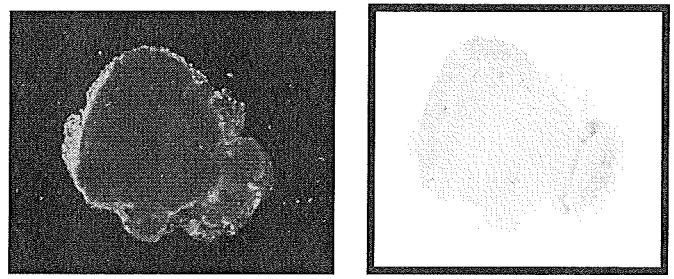
Figure 18:
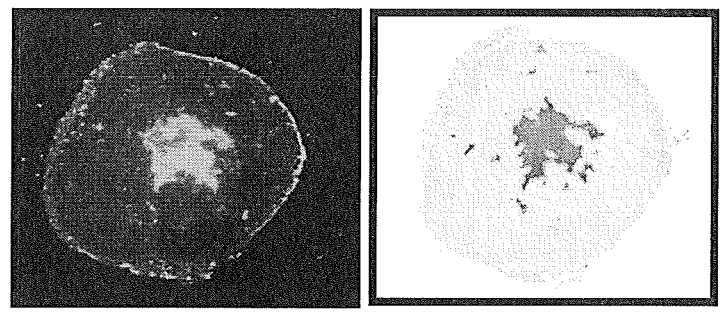

FIG. 18 is a histological examination of development of spontaneous necrosis in 4T1 tumors over time. In (a) 4T1 tumor after one week stained with HQ5 and TUNEL is shown. TUNEL staining is specific for dead cells. There is no necrosis. In (b) 4T1 tumor after 2 weeks stained with HQ5 and TUNEL is shown. Some signs of the start of Necrosis. In (c) 4T1 tumor at a later time point, e.g. 24 h, stained with HQ5 and TUNEL is shown. Clear necrosis in the center of the tumor as indicated by both HQ5 staining and TUNEL staining. 4T1 tumors spontaneously develop necrotic cores in the center of the tumor due to uncontrolled rapid growth. Necrosis can be identified by HQ5 which nicely co-localize with TUNEL staining.

The invention claimed is:

1. A method for targeting proteins in cells whose plasma membrane has lost integrity, for discriminating between live cells and cells whose plasma membrane has lost integrity, wherein the method comprises:
   (a) providing a population of cells in a tissue comprising cells whose plasma membrane has lost integrity and live cells, the cells providing a first intracellular protein;
   (b) applying a non-activated extracellularly applied compound to the population of cells, wherein the non-activated extracellularly applied compound is substantially unable to cross an intact cell membrane; wherein the non-activated extracellularly applied compound is selected from a group consisting of negatively charged non-toxic cyanine containing non-activated extracellularly applied compounds, wherein in the non-activated extracellularly applied compound the cyanine selectively interacts directly with at least one cell constituent, wherein the cell constituent is the first intracellular protein, wherein the first intracellular protein is a protein selected from the group consisting of fibrous proteins, metalloenzymes, Hsp90p co-chaperone (CDC37), binding isomers thereof, and binding decay products thereof;
   (c) targeting the cyanine of the cyanine containing non-activated extracellularly applied compound to the first intracellular protein in the cell whose plasma membrane has lost integrity, thereby forming a complex of the first intracellular protein and cyanine containing non-activated extracellularly applied compound, and
   (d) performing a measurement to determine an amount of targeted complexes formed between the cyanine of the cyanine containing non-activated extracellularly applied compound and the first intracellular protein in the cell whose plasma membrane has lost integrity thereby discriminating between live cells and cells containing the targeted complexes formed whose plasma membrane has lost integrity, wherein the measurement capable of detecting the targeted complexes formed is selected from the group consisting of: optical spectroscopies, optical microscopy, acoustical imaging, acoustic spectroscopies, Magnetic Resonance Imaging (MRI), Positron Emission Tomography (PET), Single Photon Emission Computed Tomography (SPECT), Computed Tomography (CT), and combinations thereof.

2. The method according to claim 1, wherein the first intracellular protein in claim 1, step (b) comprises 40 kDa proteins or 100 kDa proteins.

3. The method according to claim 1, wherein the cyanine is a non-activated cyanine according to FIG. 1 I, II and III,

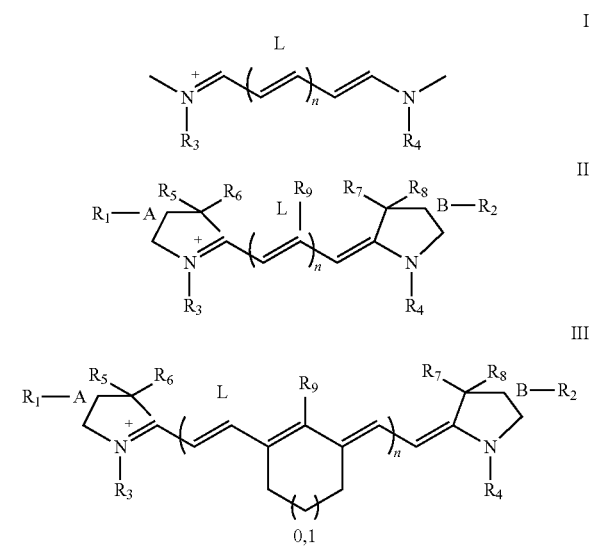

wherein
n is an integer,
the chain L has up to n−1 double bonds, wherein subfamilies II and III may comprise respectively one and two aromatic ring systems (A,B) signified by the curved line(s) C,
wherein further groups $R_5$, $R_6$, $R_7$, and $R_8$, may be present.

4. The method according to claim 1, wherein the method further comprises:
   (e) analysing the measured value in claim 1, step (d) to determine one or more parameters of the cells whose plasma membrane has lost integrity in the population of cells, and;
   (f) optionally repeating (d) and/or (e) for a given sample at multiple time-points to determine a change in the value of a parameter, or the amount of targeted complexes formed, as a function of time.

5. The method according to claim 4, wherein the one or more parameters is the presence and/or concentration and/or location of cells whose plasma membrane has lost integrity within the population of cells.

6. The method of claim 1, further comprising providing an assay for screening drugs for therapy,
wherein the amount of targeted complexes formed between the cyanine of the cyanine containing non-activated extracellularly applied compound and the first intracellular protein in the cell of claim 1, step (d) is used to screen the effectiveness of said drugs for therapy.

7. The method of claim 1, further comprising performing a diagnostic method, or monitoring a therapy,
wherein the amount of targeted complexes formed between the cyanine of the cyanine containing non-activated extracellularly applied compound and the first intracellular protein in the cell of claim 1, step (d) is used to screen the effectiveness of said diagnostic method or to monitor the effect of said therapy.

8. A complex of the negatively charged non-toxic cyanine in the cyanine containing non-activated extracellularly applied compound and the targeted first intracellular protein obtained by a method according to claim 1.

9. The complex of claim 8, having a ratio of an amount of the cyanine containing non-activated extracellularly applied compound bound to the targeted first intracellular protein contained within a given quantity of cells whose plasma membrane has lost integrity divided by an amount of the compound that is bound to a same given quantity of living cells ([amount dead cell]/[amount living cell]), wherein the ratio is larger than 10.

* * * * *